United States Patent
Aoki et al.

(10) Patent No.: US 7,714,162 B2
(45) Date of Patent: May 11, 2010

(54) BASE MULTIPLYING AGENTS AND BASE-REACTIVE CURABLE COMPOSITIONS

(75) Inventors: Kenichi Aoki, Chiba (JP); Kunihiro Ichimura, Kanagawa (JP); Motoi Nagano, Osaka (JP); Hiroji Fukui, Osaka (JP)

(73) Assignee: Sekisui Chemical Co., Ltd., Osaka (JP)

( * ) Notice: Subject to any disclaimer, the term of this patent is extended or adjusted under 35 U.S.C. 154(b) by 15 days.

(21) Appl. No.: 11/885,997

(22) PCT Filed: Mar. 6, 2006

(86) PCT No.: PCT/JP2006/304239

§ 371 (c)(1), (2), (4) Date: Sep. 10, 2007

(87) PCT Pub. No.: WO2006/095670

PCT Pub. Date: Sep. 14, 2006

(65) Prior Publication Data

US 2008/0200580 A1    Aug. 21, 2008

(30) Foreign Application Priority Data

Mar. 11, 2005 (JP) .............. 2005-070011
Feb. 21, 2006 (JP) .............. 2006-043517

(51) Int. Cl.
- C07C 269/02 (2006.01)
- C07C 271/10 (2006.01)
- C08F 2/50 (2006.01)
- C08G 65/04 (2006.01)

(52) U.S. Cl. .............. 560/163; 522/27; 522/28; 528/421

(58) Field of Classification Search .......... 522/14, 522/36, 51, 100, 27, 28; 560/16, 134, 137, 560/163; 528/421

See application file for complete search history.

(56) References Cited

FOREIGN PATENT DOCUMENTS

| JP | 2000-330270 A | 11/2000 |
|---|---|---|
| JP | 2002-128750 A | 5/2002 |
| JP | 2002-265531 A | 9/2002 |
| JP | 2003-344992 A | 12/2003 |
| JP | 2004-099579 A | 4/2004 |
| JP | 2004-250650 A | 9/2004 |
| JP | 2005-017354 A | 1/2005 |

OTHER PUBLICATIONS

Aoki et al, "Synthesis of Novel Oligomeric Base-generators to Apply to Photopolymer Systems.", Journal of Photopolymer Science and Technology, vol. 18, No. 1, May 2005, p. 133-134.*
International Search Report PCT/ISA/210 and English translation, PCT/JP2006/304239, Jun. 20, 2006 (2 pages).
JPO Office Action, App. No. 2006-043517, Aug. 1, 2006 (2 pages).

* cited by examiner

*Primary Examiner*—Mark Eashoo
*Assistant Examiner*—Michael Pepitone
(74) *Attorney, Agent, or Firm*—Cheng Law Group, PLLC

(57) ABSTRACT

To provide such a base multiplying agent capable of being used for crosslinking reaction, for example of a epoxy compound and the like, that generates another base by action of a base, and can efficiently perform base multiplying reaction, and a base-reactive curable composition using the base multiplying agent.

The base generating agent of the invention is represented by the following formula (1):

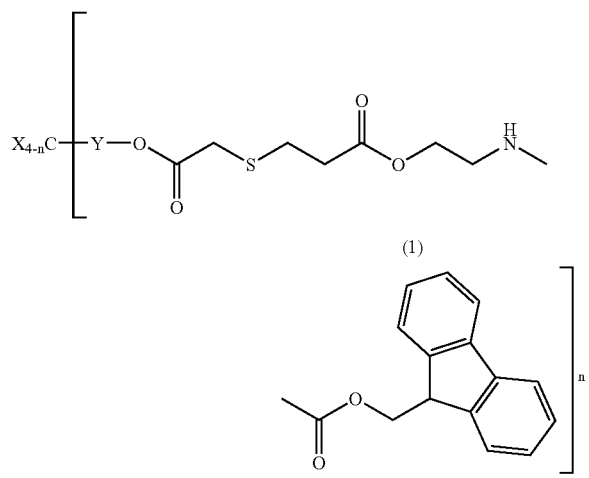

(In the formula (1), X represents a hydrogen atom, a substituted alkyl group or an unsubstituted alkyl group; Y represents a substituted or unsubstituted alkylene chain; and n represents an integer of from 1 to 4.)

9 Claims, No Drawings

BASE MULTIPLYING AGENTS AND BASE-REACTIVE CURABLE COMPOSITIONS

TECHNICAL FIELD

The present invention relates to a base multiplying agent that is decomposed by action of a base to generate another base, and more specifically, it relates to a base multiplying agent capable of being used for crosslinking reaction of a base-reactive substance, such as an epoxy compound, and a base-reactive curable composition using the base multiplying agent.

BACKGROUND ART

In recent years, a photosensitive resin composition containing an acid generating agent generating an acid upon irradiation of light is applied to various fields including a photoresist material and a photo curing material. An acid generated from an acid generating agent functions as a catalyst or a polymerization initiator.

In the case where the photosensitive resin composition is used as a photoresist material for forming a pattern, for example, an acid generating agent is irradiated with light to generate a strong acid. The strong acid generated from the acid generating agent functions as a catalyst and chemically modifies the resin component. The resin component is changed in solubility through chemical modification to form a pattern.

Various kinds of photoresist materials have been developed, and the photoresist materials are demanded to have high resolution and high sensitivity. The photoresist materials are also demanded to be capable of forming a pattern having high etching resistance. In particular, a material capable of forming a pattern having resistance to oxygen plasma etching is demanded as a deep ultraviolet ray resist material.

Various attempts for increasing a curing rate of a monomer, an oligomer, a polymer and the like have been made. The system that has been targeted for the development most frequently is a radical polymerization system, in which a radical species generated upon irradiation light is used as an initiator to polymerize numerous vinyl monomers in chains. A cationic polymerization system using an acid generated upon irradiation of light as a catalyst is also targeted for the development.

In the case of a radical polymerization system, the polymerization reaction is inhibited with oxygen in the air to decrease particularly the curing rate upon forming a thin film pattern, and therefore, it is necessary to block oxygen upon polymerization reaction. A cationic polymerization system has such an advantage that the polymerization reaction is not inhibited with oxygen in the air. However, an acid remains after curing to bring about a possibility of causing corrosion or degradation of the resin due to the acid.

Under the circumstances, such a photosensitive resin composition is strongly demanded that has high resolution and high sensitivity, is capable of forming a pattern having high etching resistance, is not inhibited in polymerization reaction with oxygen in the air, and does not generate a corrosive substance, such as a strong acid.

As a measure capable of attaining the demands, use of polymerization reaction or chemical reaction with a basic catalyst is proposed. Examples thereof include a method of using a base generating agent forming a base upon application of heat and chemically modifying a resin component with the base generated from the base generating agent as a catalyst.

An epoxy compound having an epoxy group undergoes crosslinking reaction by action of a base to be cured. Accordingly, for example, a base generating agent is irradiated with light or applied with heat to generate an amine compound in a layer containing an epoxy compound, whereby the epoxy compound can be cured by action of the amine compound as an initiator or a catalyst. However, even in the case where an amine compound is used as an initiator or a catalyst, the curing rate of the epoxy compound is low. In order to cure an epoxy compound sufficiently, a prolonged period of time is required, and it is necessary to carry out the heat treatment at a high temperature for increasing the curing rate, whereby the method has not yet been subjected to practical use.

Non-patent Document 1 shown below discloses base multiplying reaction capable of secondarily multiplying a basic compound generated by action of light. Patent Document 1 and Patent Document 2 shown below disclose a photosensitive composition containing a base multiplying agent, which is a urethane compound undergoing base multiplying reaction.

Patent Document 1: JP-A-2000-330270

Patent Document 2: JP-A-2002-128750

Non-patent Document 1: M. Miyamoto, K. Arimitsu and K. Ichimura, J. Photopolym. Sci. Technol., 12, 315 (1999), K. Arimitsu, M. Miyamoto and K. Ichimura, J. Photopolym. Sci. Technol., 12, 317 (1999), K. Arimitsu, M. Miyamoto and K. Ichimura, Angew. Chem., Int. Ed., 39, 3425 (2000)

DISCLOSURE OF THE INVENTION

The bases generated in the base multiplying reaction disclosed in Non-patent Document 1 and Patent Documents 1 and 2 shown above are mainly primary or secondary aliphatic amines. Upon constituting a photosensitive composition, a base multiplying agent generating the amines is used in combination, for example, with a photo base generating agent or a base reactive substance.

In order to perform base multiplying reaction in a photosensitive composition efficiently, it is generally necessary to carry out a heat treatment. In the case where base multiplying reaction is conducted in an open system, however, an amine generated through base multiplying reaction is liable to be vaporized and diffused in the process of the heat treatment. For example, in the case where an epoxy compound is cured by action of an amine, even when a large amount of a base multiplying agent is added, there are cases where the effect of the addition thereof cannot be sufficiently enjoyed. The urethane compounds disclosed in Patent Documents 1 and 2 are low in solubility in an organic solvent. For example, the urethane compound fails to have a sufficient solubility in an epoxy compound in a liquid state with relatively low polarity. Furthermore, in the case where a pattern is formed by using a photosensitive composition containing the base multiplying agent as a photoresist material, the base multiplying agent itself is demanded not to impair the etching resistance capability of the pattern.

In view of the current circumstances of the related art, an object of the invention is to provide such a base multiplying agent capable of being used for crosslinking reaction, for example of a epoxy compound and the like, that generates another base by action of a base, and can efficiently perform base multiplying reaction, and a base-reactive curable composition using the base multiplying agent.

The base generating agent of the invention is represented by the following formula (1):

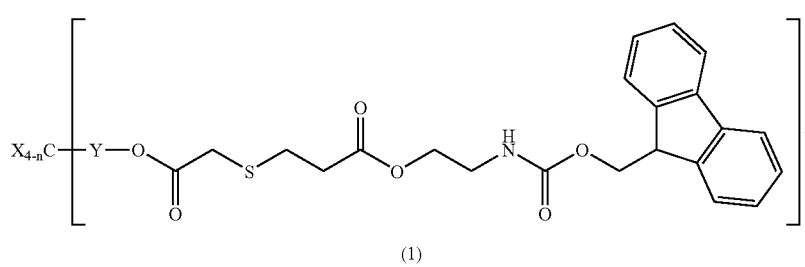

[Chem. 1]

(1)

(In the formula (1), X represents a hydrogen atom, a substituted alkyl group or an unsubstituted alkyl group; Y represents a substituted or unsubstituted alkylene chain; and n represents an integer of from 1 to 4.)

According to one specific aspect of the base multiplying agent of the invention, in the formula (1), Y represents a methylene chain.

According to another specific aspect of the base multiplying agent of the invention, in the formula (1), X represents an ethyl group.

According to still another specific aspect of the base multiplying agent of the invention, in the formula (1), n represents 3.

According to a further specific aspect of the base multiplying agent of the invention, in the formula (1), n represents 4.

The base-reactive curable composition of the invention is characterized by containing the base multiplying agent represented by the formula (1), a base generating agent, and a curable compound cured by action of a base.

According to one specific aspect of the base-reactive curable composition of the invention, the curable compound is an epoxy compound.

According to another specific aspect of the base-reactive curable composition of the invention, the epoxy compound is a liquid epoxy resin.

According to still another specific aspect of the base-reactive curable composition of the invention, the base generating agent is a photo base generating agent generating a base by irradiation of light.

ADVANTAGE OF THE INVENTION

The base multiplying agent of the invention represented by the formula (1) has a carbamate group and undergoes structural change to generate a base in a multiplying manner. Accordingly, in the case where the base multiplying agent is present, for example, in a base-reactive substance, such as an epoxy compound reacting with an amine or the like, it can effectively cure the epoxy compound.

In the case where X represents an ethyl group in the formula (1), the base multiplying reaction is effectively facilitated owing to the small steric hindrance of X.

In the case where Y represents a methylene chain in the formula (1), the base multiplying reaction is effectively facilitated owing to the small steric hindrance of Y.

In the case where X represents an ethyl group, Y represents a methylene chain, and n represents 3 in the formula (1), the base multiplying reaction is further effectively facilitated owing to the three carbamate groups present in one molecule.

In the case where Y represents a methylene chain, and n represents 4 in the formula (1), the base multiplying reaction is further effectively facilitated owing to the four carbamate groups present in one molecule.

The base-reactive curable composition of the invention contains a base multiplying agent represented by the formula (1), a base generating agent, and a curable compound cured by action of a base. When the base-reactive curable composition is irradiated with light or applied with heat, a base is generated from the base generating agent. The base generated from the base generating agent functions as a catalyst, and another base is generated from the base multiplying agent. The curable compound is cured by action of the bases generated from the base generating agent and the base multiplying agent. Accordingly, the base-reactive curable composition of the invention is excellent in curing property since the base generating agent and the base multiplying agent generate a large amount of base.

In the case where the curable compound is an epoxy resin, crosslinking reaction of the epoxy compound efficiently proceeds by action of the base to exhibit excellent curing property.

In the case where the epoxy compound is a liquid epoxy resin, high curing property can be obtained with a liquid epoxy resin, but not a solid one, by using the base multiplying agent of the invention. A liquid epoxy resin is inferior in curing property to a solid epoxy resin, but a large amount of base is generated in a multiplying manner from the base multiplying agent to increase the curing rate of the liquid epoxy resin.

In the case where the base generating agent is a photo base generating agent generating a base by irradiation of light, there is no necessity of carrying out a heat treatment at a high temperature for generating a base. In the case where the curing reaction is conducted in an open system, the generated base, such as an amine, is hard to be vaporized and diffused, and thus the curing reaction proceeds further efficiently.

BEST MODE FOR CARRYING OUT THE INVENTION

The invention will be described in detail.

The base multiplying agent of the invention is a compound represented by the formula (1). The base multiplying agent of the invention is decomposed through base multiplying reaction to generate another amine. The generated amine functions as another catalyst to generate a large amount of amine in a multiplying manner.

In the formula (1), X represents a hydrogen atom, a substituted alkyl group or an unsubstituted alkyl group.

Specific examples of X in the formula (1) include a methyl group, an ethyl group and a propyl group. X is preferably an unsubstituted alkyl group since the base multiplying reaction occurs efficiently. In particular, X is more preferably an ethyl group since the steric hindrance of X is decreased to facilitate the base multiplying reaction further effectively.

In the formula (1), Y represents a substituted or unsubstituted alkylene chain.

Specific examples of Y in the formula (1) include a methylene chain, an ethylene chain and a propylene chain. Y is preferably an unsubstituted alkylene chain since the base multiplying reaction occurs efficiently. In particular, Y is more preferably a methylene chain since the steric hindrance of Y is decreased to facilitate the base multiplying reaction further effectively.

In the formula (1), n represents an integer of from 1 to 4. In the case where the base multiplying agent represented by the formula (1) has plural carbamate groups in one molecule, the base multiplying reaction is facilitated further effectively by catalytic action of the generated base. Accordingly, in the formula (1), n preferably represents an integer of 3 or 4.

Specific examples of the compound represented by the formula (1) include compounds represented by formulae (2) and (3) below.

[Chem. 2]

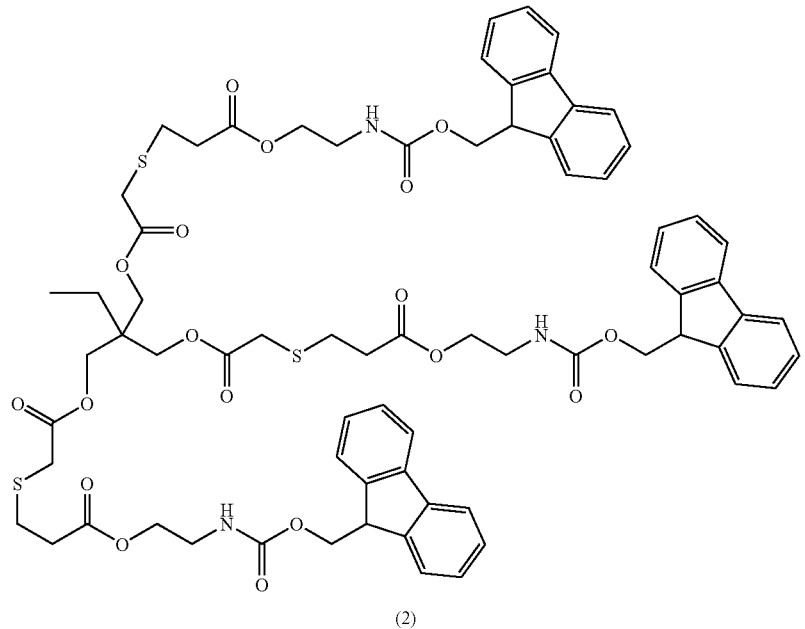

(2)

[Chem. 3]

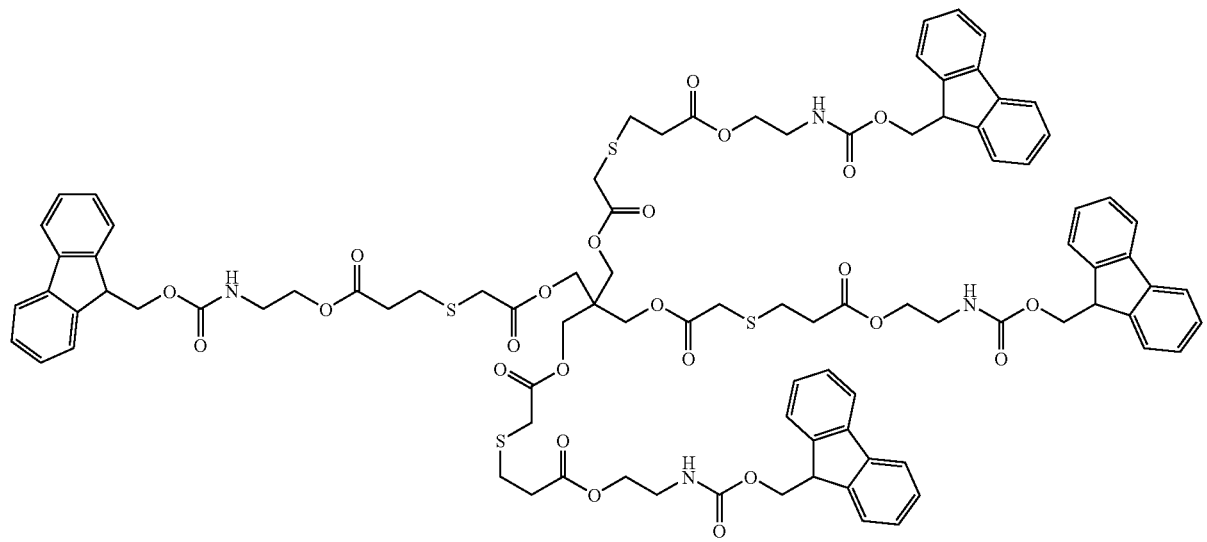

(3)

The base multiplying agents represented by the formula (2) and the formula (3) each has plural carbamate groups in one molecule. Accordingly, these compounds have such characteristics that the base multiplying reaction is facilitated to proceed by catalytic action of the generated base.

In the base multiplying reaction of the base multiplying agent of the invention, an active hydrogen atom is withdrawn with a base to generate a carbanion. Subsequently, carbamic acid is released, and decomposition further proceeds to generate a base and carbon dioxide. The base multiplying reaction of the base multiplying agent is shown by the formula (4) with reference to the base multiplying agent represented by the formula (2) as an example. As shown in the formula (4), in the base multiplying reaction, an amine compound, carbon dioxide and an olefin are generated from the base multiplying agent.

The base multiplying agent of the invention is synthesized, for example, through addition reaction of fluorenylmethanol and an isocyanate derivative, or addition reaction of an acrylate monomer having a fluorenylcarbamate group and a polythiol derivative, while not particularly limited. In the former addition reaction, the compound can be simply synthesized by properly using a tin catalyst. In the later addition reaction, the compound can be simply synthesized by properly using a basic catalyst.

The base-reactive curable composition of the invention contains a base multiplying agent represented by the formula (1), a base generating agent, and a curable compound cured by action of a base.

The mixing ratio of the base multiplying agent is preferably in a range of from 10 to 45% by weight based on 100% by weight of the base-reactive curable composition. In the case where the base multiplying agent is less than 10% by

[Chem. 4]

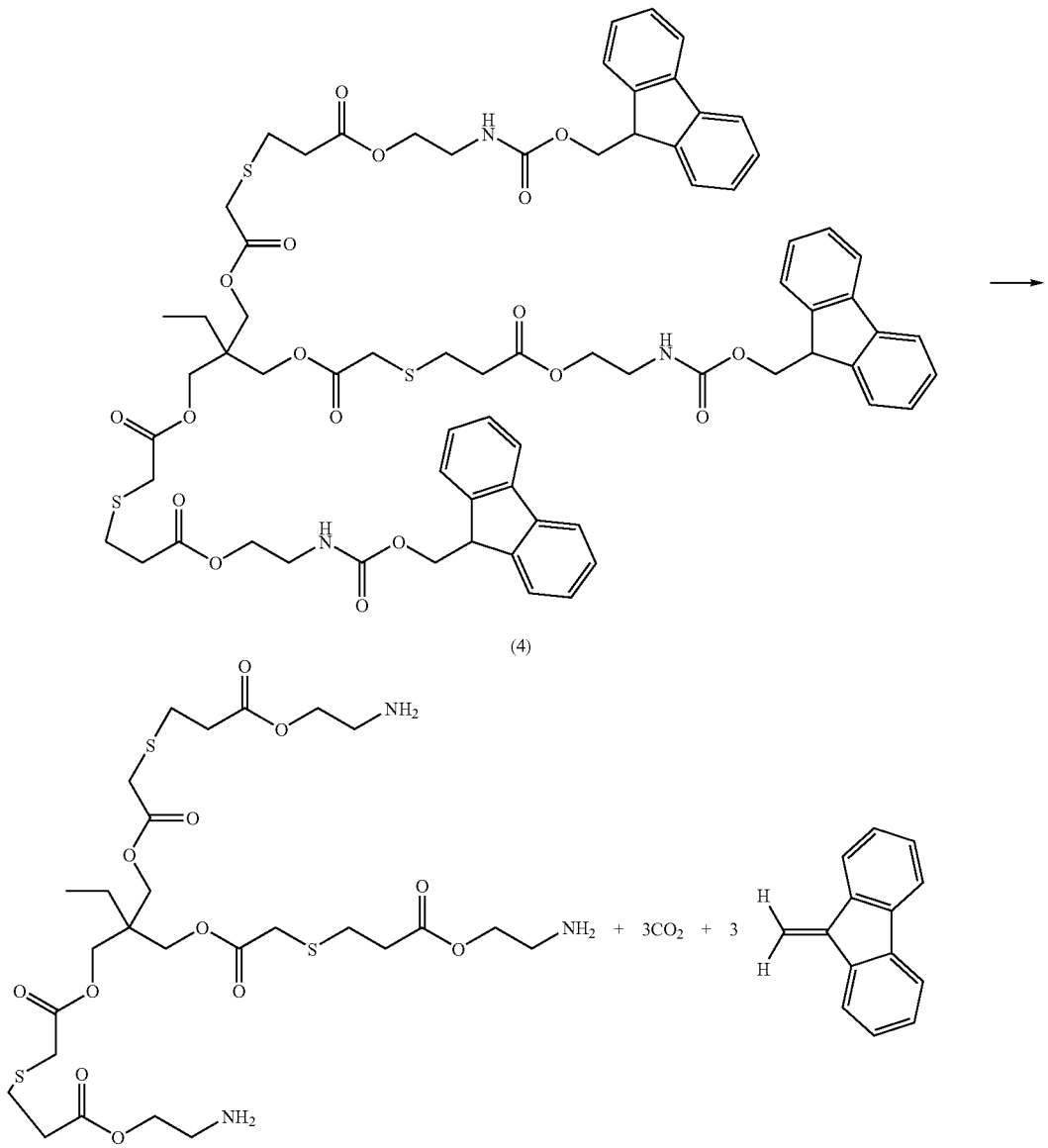

weight, the amount of the base generated through the base multiplying reaction is small to bring about some cases where the curing rate is deteriorated. In the case where the base multiplying agent exceeds 45% by weight, there are cases where the base multiplying agent is deposited in the coated film.

The base generating agent is such a substance that generates a base upon irradiation of light or application of heat. The base generating agent is preferably a photo base generating agent generating a base upon irradiation of light or a thermal latent base generating agent generating a base upon application of heat, while not particularly limited. In particular, a photo base generating agent is more preferably used since there is no necessity of carrying out a heat treatment at a high temperature for generating a base.

The photo base generating agent is not particularly limited, and examples thereof include an o-nitrobenzyl type photo base generating agent, a (3,5-dimethoxybenzyloxy)carbonyl type photo base generating agent, an amyloxyimino group type photo base generating agent and a dihydropyridine type photo base generating agent, which have been known in the art. In particular, an o-nitrobenzyl type photo base generating agent is more preferably used since it is excellent in base generating efficiency and simplicity of synthesis.

The thermal latent base generating agent is not particularly limited, and preferred examples thereof include a salt of an organic acid and a base decomposed through decarboxylation upon heating, a compound releasing an amine compound by decomposition through intramolecular nucleophilic substitution reaction, Lossen rearrangement reaction or Beckmann rearrangement reaction, and a compound releasing a base through certain reaction upon heating. In particular, a salt of an organic acid and a base decomposed through decarboxylation upon heating is preferably used since it is excellent in base generating efficiency.

Examples of the thermal latent base generating agent include a salt of tricholoacetic acid disclosed in British Patent No. 998,949, a salt of α-sulfonylacetic acid disclosed in U.S. Pat. No. 4,060,420, a salt of propionic acid compound disclosed in JP-A-59-157637, a 2-carboxylcarboxyamide derivative, a salt of a thermal decomposing acid and an organic base with an alkali metal and an alkaline earth metal as a base component disclosed in JP-A-59-168440, a hydroxamcarbamate compound utilizing Lossen rearrangement disclosed in JP-A-59-180537, an aldoxime carbamate compound generating nitrile upon heating disclosed in JP-A-59-195237, and thermal base generating agents disclosed in British Patent No. 998,945, U.S. Pat. No. 3,220,846, British Patent No. 279,480, JP-A-50-22625, JP-A-61-32844, JP-A-61-51139, JP-A-61-52638, JP-A-61-51140, JP-A-61-53634, JP-A-61-53640, JP-A-61-55644, JP-A-61-55645 and the like.

Specific examples of the thermal latent base generating agent include guanidine trichloroacetate, methylguanidine trichloroacetate, potassium trichloroacetate, guanidine phenylsulfonylacetate, guanidine p-chlorophenylsulfonylacetate, guanidine p-methanesulfonylphenylsulfonylacetate, potassium phenylpropiolate, guanidine phenylpropiolate, cesium phenylpropiolate, guanidine p-chlorophenylpropiplate, guanidine p-phenylene-phenylpropiolate, tetramethylammonium phenylsulfonylacetate and tetramethylammonium phenylpropiolate.

The mixing ratio of the base generating agent is preferably in a range of from 1 to 30% by weight based on 100% by weight of the base-reactive curable composition. In the case where the base generating agent is less than 1% by weight, the amount of the base generated from the base generating agent is too small to bring about some cases where the advantage of addition of the base multiplying agent cannot be sufficiently obtained. In the case where the base generating agent exceeds 30% by weight, there are cases where it is excessive for obtaining the advantage of addition of the base generating agent.

The curable compound undergoes crosslinking reaction, which proceeds by action of a base generated from the base generating agent and the base multiplying agent, to be cured. The curable compound is not particularly limited, and examples thereof include an epoxy compound, an acrylate oligomer and an isocyanate oligomer. In particular, an epoxy compound is preferably used since crosslinking reaction efficiently proceeds by action of a base.

As the epoxy compound, any of a high viscosity or solid epoxy resin and a liquid epoxy resin may be used. In particular, a liquid epoxy resin is preferably used. A liquid epoxy resin is excellent in handleability but is inferior in curing property to a solid epoxy resin. However, a liquid epoxy resin can provide a base-reactive curable composition having high curing property by using the base multiplying agent of the invention.

The high viscosity or solid epoxy resin is not particularly limited, and examples thereof include BPF type epoxy resin, BPA type Epoxy Resin, BPF type Epoxy Resin, Novolak type Epoxy Resin, Brominated Epoxy Resin and Flexible Epoxy Resin disclosed in brochure of Tohto Kasei Co., Ltd., Epikote Basic Solid type and Epikote Bis-F Solid type disclosed in brochure of Yuka-Shell Epoxy Co., Ltd., and EHPE Alicyclic Solid Epoxy Resin disclosed in brochure of Daicel Chemical Industries, Ltd. In particular, a bisphenol type epoxy resin and a novolak type epoxy resin are more preferably used since a tough coated film can be obtained.

In the case where the high viscosity or solid epoxy resin is used, a monofunctional epoxy compound is preferably contained as a reactive diluent. Examples of the monofunctional epoxy compound include EX-111, EX-121, EX-141, EX-145, EX-146, EX-171, EX-192, EX-111 and EX-147, which are Denacol series disclosed in brochure of Nagase Chemtex Corp. and M-1230, EHDG-L and 100MF, which are Epolight series disclosed in brochure of Kyoeisha Chemical Co., Ltd.

The liquid epoxy resin is not particularly limited, and examples thereof include EX-611, EX-612, EX-614, EX-614B, EX-614, EX-622, EX-512, EX-521, EX-411, EX-421, EX-313, EX-314, EX-321, EX-201, EX-211, EX-212, EX-252, EX-810, EX-811, EX-850, EX-851, EX-821, EX-830, EX-832, EX-841, EX-861, EX-911, EX-941, EX-920, EX-721, EX-221, EM-150, EM-101 and EM-103, which are Denacol series disclosed in brochure of Nagase Chemtex Corp., YD-115, YD-115G, YD-115CA, YD-118T and YD-127 disclosed in brochure of Tohto Kasei Co., Ltd., and 40E, 100E, 200E, 400E, 70P, 200P, 400P, 1500NP, 1600, 80MF, 100MF, 4000, 3002 and 1500, which are Epolight series disclosed in brochure of Kyoeisha Chemical Co., Ltd.

Examples of the liquid epoxy resin further include Celloxide 2021, Celloxide 2080, Celloxide 3000, Epolead GT300, Epolead GT400, Epolead D-100ET, Epolead D-100OT, Epolead D-100DT, Epolead D-100ST, Epolead D-200HD, Epolead D-200E, Epolead D-204P, Epolead D-210P, Epolead D-210P, Epolead PB3600 and Epolead PB4700, which are alicyclic epoxy compounds, disclosed in brochure of Daicel Chemical Industries, Ltd.

In particular, an epoxy compound having three or more glycidyl groups is more preferably used as the epoxy compound since it is excellent in curing property.

The mixing ratio of the curable compound is preferably in a range of from 50 to 80% by weight based on 100% by weight of the base-reactive curable composition. In the case where the curable compound is less than 50% by weight, there are cases where the base generating agent and the base multiplying agent are deposited in the coated film. In the case where the curable compound exceeds 80% by weight, there are cases where the curing property is deteriorated.

The base-reactive curable composition preferably contains a sensitizing agent. The base-reactive curable composition containing a sensitizing agent is improved in sensitivity.

The sensitizing agent is not particularly limited, and examples thereof include benzophenone, p,p'-tetramethylaminobenzophenone, p,p'-tetraethylaminobenzophenone, 2-chlorothioxanthone, anthrone, 9-ethoxyanthracene, anthracene, pyrene, perylene, phenothiazine, benzyl, acridine orange, benzoflavin, setoflavin-T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3,3'-carbonyl-bis(5,7-dimethoxycarbonylcoumarin) and coronene. The sensitizing agents may be used solely or in combination of plural kinds thereof.

The mixing ratio of the sensitizing agent is preferably in a range of from 1 to 20% by weight based on 100% by weight of the base-reactive curable composition. In the case where the sensitizing agent is less than 1% by weight, there are cases where the sensitivity cannot be sufficiently improved. In the case where the sensitizing agent exceeds 20% by weight, there are cases where it is excessive for improving the sensitivity.

The base-reactive curable composition may contain a solvent. The base-reactive curable composition can be improved in coating property by mixing a solvent.

The solvent is not particularly limited, and examples thereof include an aromatic hydrocarbon compound, such as benzene, xylene, toluene, ethylbenzene, styrene, trimethylbenzene and diethylbenzene; a saturated or unsaturated hydrocarbon compound, such as cyclohexane, cyclohexene, dipentene, n-pentane, isopentane, n-hexane, isohexane, n-heptane, isoheptane, n-octane, isooctane, n-nonane, isononane, n-decane, isodecane, tetrahydronaphthalene and squalene; an ether compound, such as diethyl ether, di-n-propyl ether, diisopropyl ether, dibutyl ether, ethyl propyl ether, diphenyl ether, diethylene glycol dimethyl ether, diethylene glycol diethyl ether, diethylene glycol dibutyl ether, diethylene glycol methyl ethyl ether, dipropylene glycol dimethyl ether, dipropylene glycol diethyl ether, dipropylene glycol dibutyl ether, dipropylene glycol methyl ethyl ether, ethylene glycol dimethyl ether, ethylene glycol diethyl ether, ethylene glycol dipropyl ether, ethylene glycol methyl ethyl ether, tetrahydrofuran, 1,4-dioxane, propylene glycol monomethyl ether acetate, ethylene glycol monoethyl ether acetate, dipropylene glycol methyl ether acetate, diethylene glycol monoethyl ether acetate, ethylcyclohexane, methylcyclohexane, p-menthane, o-menthane, m-menthane, dipropyl ether and dibutyl ether; a ketone compound, such as acetone, methyl ethyl ketone, methyl isobutyl ketone, diethyl ketone, dipropyl ketone, methyl amyl ketone, cyclopentanone, cyclohexanone and cycloheptanone; and an ester compound, such as ethyl acetate, methyl acetate, butyl acetate, propyl acetate, cyclohexyl acetate, methyl cellosolve acetate, ethyl cellosolve acetate, butyl cellosolve acetate, ethyl lactate, propyl lactate, butyl lactate, isoamyl lactate and butyl stearate. The solvents may be uses solely or in combination of plural kinds thereof.

The mixing ratio of the solvent may be appropriately selected, for example, in such a manner that the base-reactive curable composition can be coated uniformly upon forming a base-reactive curable composition layer by coating the composition.

Other additives may be added to the base-reactive curable composition depending on necessity. Examples of the additives include a filler, a pigment, a dye, a leveling agent, a defoaming agent, an antistatic agent, an ultraviolet ray absorbent, a pH controlling agent, a dispersant, a dispersion assistant, a surface modifier, a plasticizer, a plasticization accelerator and a dripping preventing agent.

As having been described, the base-reactive curable composition is constituted by using the base multiplying agent of the invention, a photo base generating agent and a curable compound, such as an epoxy compound. The base-reactive curable composition can be suitably used, for example, as a high sensitivity ultraviolet ray curable material and a high sensitivity resist material.

The invention will be described in more detail with reference to examples below, but the invention is not limited to the examples.

Example 1

Synthesis of Base Multiplying Agent Flu3

The base multiplying agent Flu3 represented by the formula (2) was synthesized according to the following (A) to (C) in this order.

(A) Synthesis of Fluorenylmethanol

Fluorenylmethanol was synthesized according to the formula (5) below.

[Chem. 5]

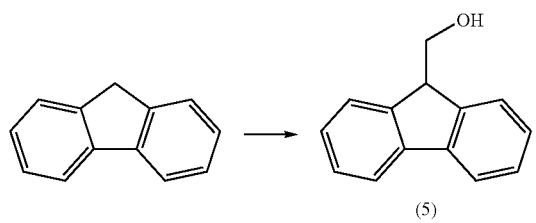

(5)

60 g (0.36 mol) of fluorine was dissolved in 1,500 mL of dehydrated THF. Thereafter, 225 mL of a butyllithium hexane solution (1.6 M) was slowly added dropwise thereto at 0° C. in an argon gas atmosphere. 12 g of p-formaldehyde was then added, followed by stirring at room temperature for 5 hours. After stirring, 600 mL of a saturated sodium bicarbonate water was added, the mixture was extracted with diethyl ether, and the organic layer was washed twice with saturated saline. After drying over anhydrous magnesium sulfate, the solvent was distilled off. The resulting solid in a paste form was recrystallized from a mixed solvent of hexane and ethanol to obtain 50 g of fluorenylmethanol in a white acicular crystal form. It was confirmed that the resulting compound had the aforementioned structure represented by the formula (5) by measuring with $^1$H-NMR. The melting point and the measurement result of $^1$H-NMR are shown below.

Yield: 71%

Melting point: 98-101° C.

$^1$H-NMR (270 MHz, CDCl$_3$) δ (ppm): 1.71 (1H, s, OH), 3.6-4.3 (3H, m, CH, CH$_2$), 7.2-7.5 (4H, m, ArH), 7.54 (2H, d, J=7.3 Hz, ArH), 7.73 (2H, d, J=7.3 Hz, ArH)

(B) Synthesis of Acrylate Monomer

An acrylate monomer was synthesized according to the formula (6) below.

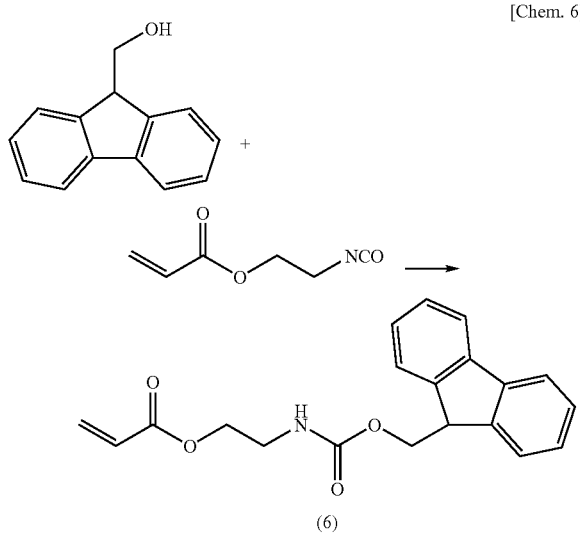

(6)

60 mL of dehydrated benzene and 100 mg of di-n-butyltin dilaurylate as a catalyst were added to 2.08 g (10.6 mmol) fluorenylmethanol synthesized according to the formula (5). Thereafter, 1.41 g (10 mmol) of 2-isocyanatoethyl acrylate and 20 mL of a benzene solution containing 50 mg of 2,6-di-tert-butyl-p-cresol as a polymerization inhibitor were slowly added dropwise thereto under refluxing. After refluxing for 9 hours, the mixture was cooled to room temperature, and the solvent was distilled off. A small amount of diethyl ether and a large amount of hexane were added to the resulting brown oil. Recrystallization was effected by storing in a freezer to obtain an acrylate monomer in a white crystal form. It was confirmed that the resulting compound had the aforementioned structure represented by the formula (6) by measuring with $^1$H-NMR. The melting point and the measurement result of $^1$H-NMR are shown below.

Yield: 71%

Melting point: 101-103° C.

$^1$H-NMR (270 MHz, CDCl$_3$) δ (ppm): 3.3-3.7 (2H, m, NH—CH$_2$), 4.0-4.6 (4H, m, O—CH$_2$), 5.06 (1H, s, NH), 5.85 (1H, d, J=10.3 Hz, C=CH$_2$), 6.0-6.2 (1H, m, C=CH), 6.44 (1H, d, J=17.0 Hz, C=CH$_2$), 7.1-7.5 (4H, m, ArH), 7.57 (2H, d, J=7.3 Hz, ArH), 7.76 (2H, d, J=7.3 Hz, ArH)

(C) Synthesis of Base Multiplying Agent Flu3

The base multiplying agent Flu3 was synthesized according to the formula (7) below.

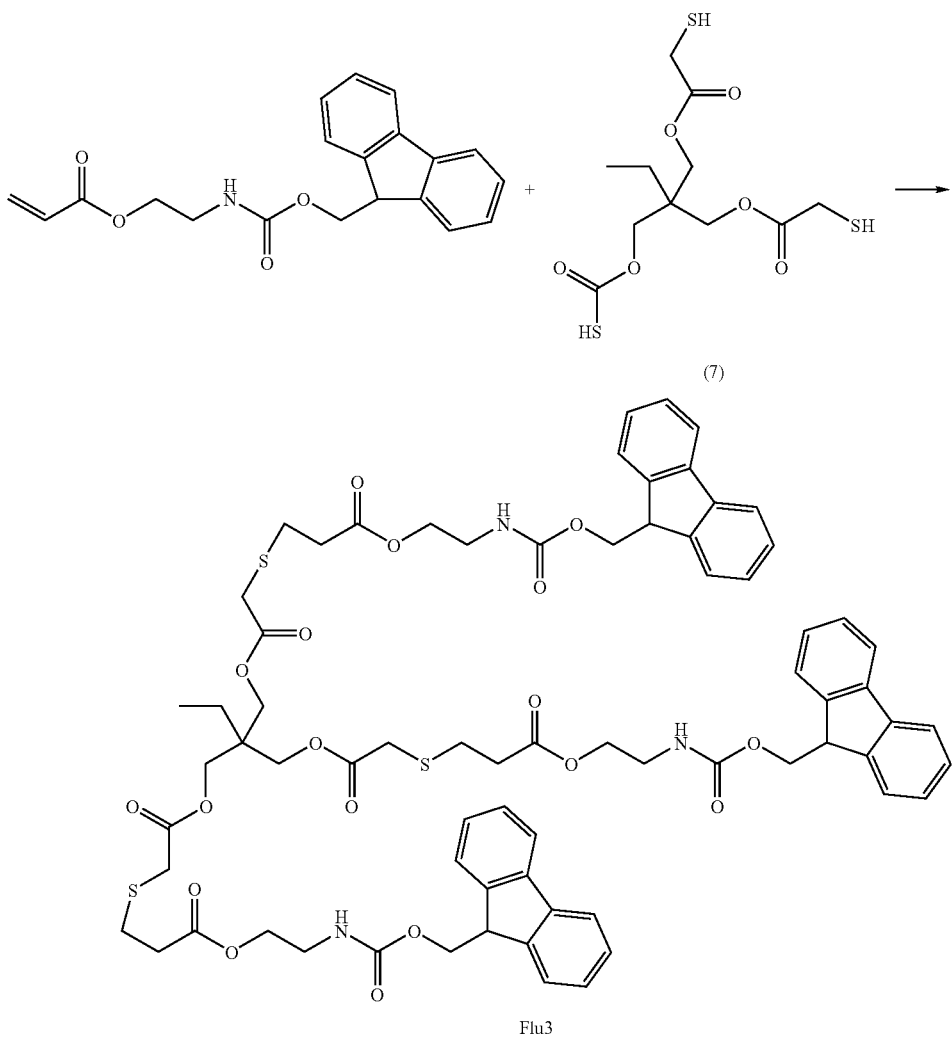

(7)

Flu3

0.36 g (1.0 mmol) of the acrylate monomer synthesized according to the formula (6), 1.0 g (3.0 mmol) of TMTG (trithiol derivative) and 19 mg (0.1 mmol) of tri-n-butylamine as a catalyst were dissolved in 7 mL of dehydrated dichloromethane, and the solution was stirred at room temperature for 4 days. After stirring, the solution was washed with 2M hydrochloric acid and then saturated saline, and dried over anhydrous magnesium sulfate. Thereafter, an oil obtained by distilling the solvent off under reduced pressure was frozen in a freezer to obtain Flu3. It was confirmed that the resulting compound had the aforementioned structure represented by the formulae (2) and (7) by measuring with $^1$H-NMR and MALDI. The measurement result of $^1$H-NMR and MALDI are shown below.

Yield of Colorless Oil: 89%

$^1$H-NMR (270 MHz, CDCl$_3$) δ (ppm): 0.8-1.2 (3H, m, CH$_3$), 1.4-1.6 (2H, m, CH$_2$), 2.5-2.8 (6H, m, CH$_2$), 2.8-3.1 (6H, m, CH$_2$), 3.2-3.6 (12H, m, CH$_2$), 4.0-4.6 (18H, m, CH$_2$), 5.2-5.5 (3H, m, NH), 7.2-7.5 (12H, m, ArH), 7.58 (6H, d, J=7.3 Hz, ArH), 7.74 (6H, d, J=7.3 Hz, ArH)

MALDI (m/z): 1390.1 (M+Na)$^+$), 1406.1 (M+K)$^+$)

Example 2

Synthesis of Base Multiplying Agent Flu4

The base multiplying agent Flu4 represented by the formula (3) was synthesized according to the following manner. The base multiplying agent Flu4 was synthesized according to the formula (8) below.

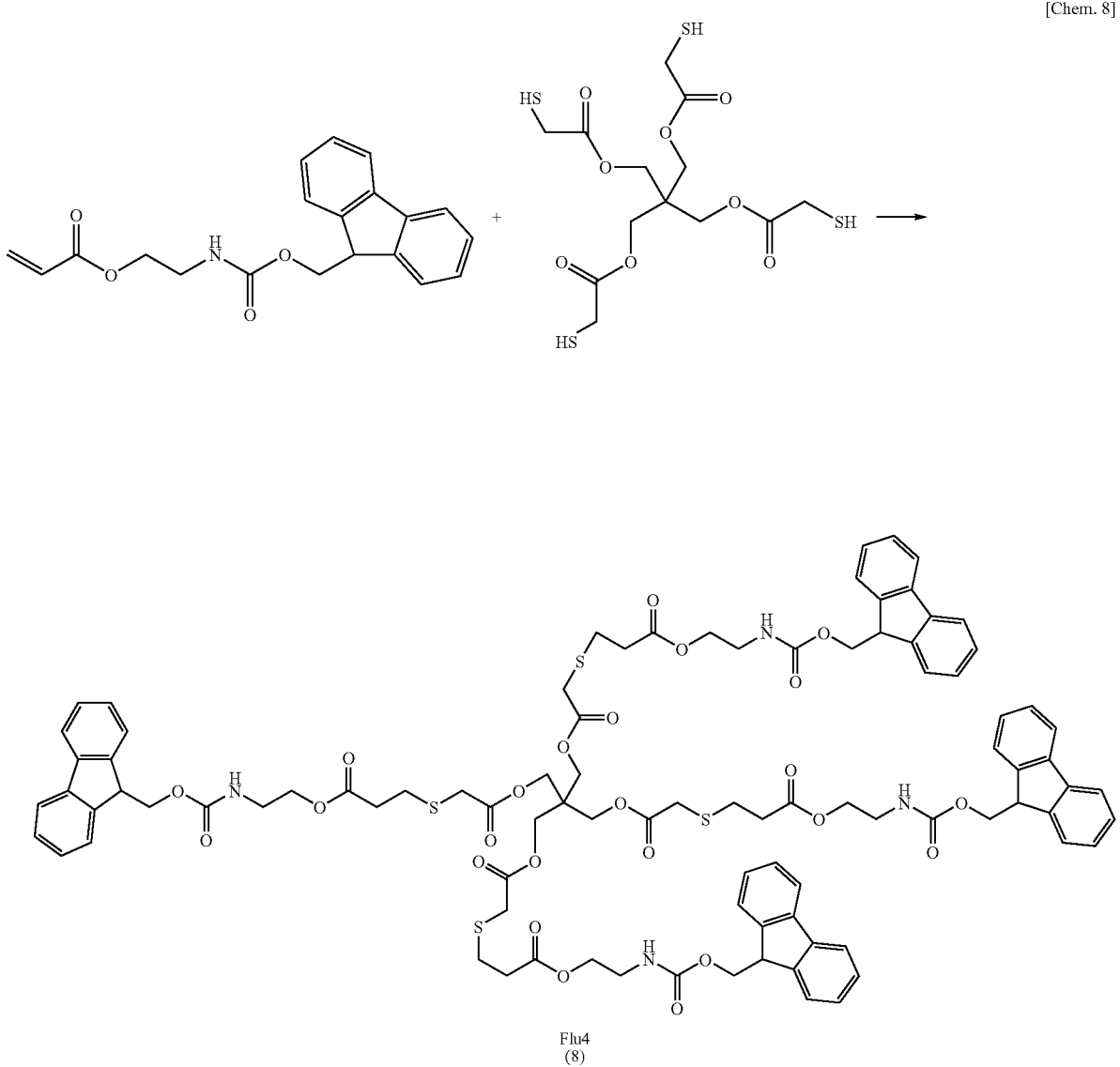

Flu4
(8)

2.0 g (6.0 mmol) of the acrylate monomer synthesized according to the formula (6) in Example 1, 0.65 g (1.5 mmol) of PETG (tetrathiol derivative) and 40 mg of tri-n-butylamine as a catalyst were dissolved in 15 mL of dehydrated dichloromethane, and the solution was stirred at room temperature for 3 days. After stirring, the solution was washed with 2M hydrochloric acid and then saturated saline, and dried over anhydrous magnesium sulfate. Thereafter, an oil obtained by distilling the solvent off under reduced pressure was frozen in a freezer to obtain Flu4. It was confirmed that the resulting compound had the aforementioned structure represented by the formulae (3) and (8) by measuring with $^1$H-NMR and MALDI. The measurement result of $^1$H-NMR and MALDI are shown below.

Colorless Oil
 Yield: 72%
 $^1$H-NMR (270 MHz, CDCl$_3$) δ (ppm): 2.5-2.8 (8H, m, CH$_2$), 2.8-3.1 (8H, m, CH$_2$), 3.2-3.6 (16H, m, CH$_2$), 4.0-4.6 (24H, m, CH$_2$), 5.3-5.5 (4H, m, NH), 7.2-7.5 (16H, m, ArH), 7.60 (8H, d, J=7.3 Hz, ArH), 7.77 (8H, d, J=7.3 Hz, ArH)
 MALDI (m/z): 1804.5 (M+Na)$^+$, 1820.5 (M+K)$^+$ Comparative Example 1

Synthesis of Base Multiplying Agent Flu2

A base multiplying agent Flu2 was synthesized according to the formula (9) below.

60 mL of dehydrated benzene and 100 mg of di-n-butyltin dilaurylate as a catalyst were added to 7.85 g (40 mmol) fluorenylmethanol synthesized according to the formula (5) in Example 1. Thereafter, 20 mL of a benzene solution of 4.21 g (20 mmol) of trimethylhexylisocyanate was slowly added dropwise thereto under refluxing. After refluxing for 7 hours, the mixture was cooled to room temperature, and the solvent was distilled off. A small amount of diethyl ether and a large amount of hexane were added to the resulting brown oil. Recrystallization was effected by storing in a freezer to obtain a compound Flu2 in a white crystal form. It was confirmed that the resulting compound Flu2 had the aforementioned structure represented by the formula (9) by measuring with $^1$H-NMR and ESI-MS. The melting point and the measurement results of $^1$H-NMR and ESI-MS are shown below.

(Flu2)
 Yield: 93%
 Melting point: 72-74° C.
 $^1$H-NMR (270 MHz, CDCl$_3$) δ (ppm): 0.7-1.8 (14H, m, CH$_2$, CH$_3$), 2.8-3.3 (4H, m, NH—CH$_2$), 4.19 (2H, s, fluorene CH), 4.2-4.5 (4H, m, O—CH$_2$), 4.6-5.3 (2H, m, NH), 7.2-7.4 (8H, m, ArH), 7.57 (4H, d, J=7.3 Hz, ArH), 7.73 (4H, d, J=7.3 Hz, ArH)
 ESI-MS (m/z): 625.4 (M+Na)$^+$ (Photo Base Generating Agent)
 A compound PBG-2 represented by the formula (10) below was prepared as a photo base generating agent.

[Chem. 9]

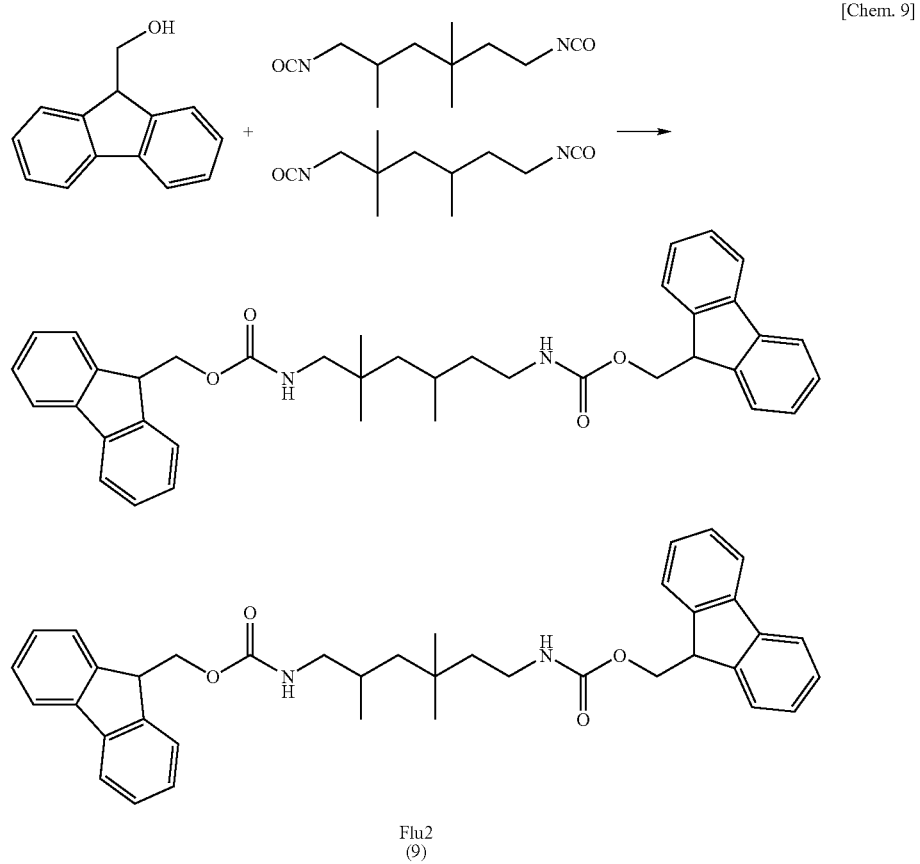

Flu2
(9)

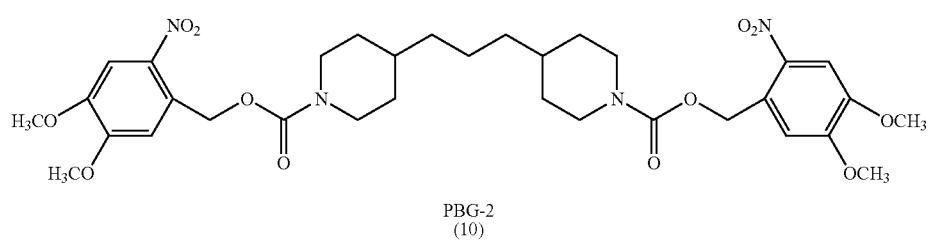

PBG-2
(10)

(Synthesis of Bispiperidyl Type Photo Base Generating Agent PBG-2)

The photo base generating agent PBG-2 represented by the formula (10) was synthesized in the following manner.

(A-1) Synthesis of 2-Nitro-4,5-dimethoxybenzyl-4'-nitrophenyl Carbonate

2-Nitro-4,5-dimethoxybenzyl-4'-nitrophenyl carbonate was synthesized according to the formula (11) below.

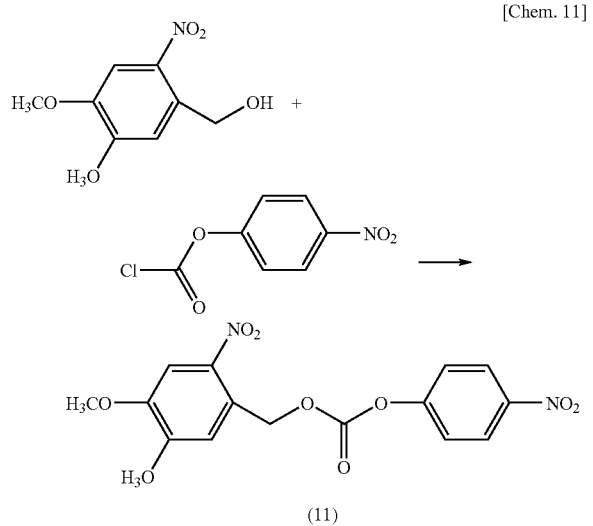

(11)

9.4 g (44 mmol) of o-nitro-4,5-dimethoxybenzyl alcohol and 4.8 g (47 mmol) of triethylamine were dissolved in 50 mL of a mixed solvent of THF and dichloromethane (1/1 (v/v)). Thereafter, 20 mL of a THF solution of 10.3 g (48 mmol) of 4-nitrophenyl chloroformate was slowly added thereto dropwise at 0° C. under an argon atmosphere. After completing dropwise addition, introduction of argon gas was terminated, and the mixture was refluxed for 10 hours. The solution was cooled to room temperature, and the solvent was distilled off. Dichloromethane was then added to the solution, which was washed with water three times. The solution was dried over anhydrous magnesium sulfate, and the solvent was distilled off. Recrystallization was effected from a mixed solvent of ethanol and toluene to obtain 2-nitro-4,5-dimethoxybenzyl-4'-nitrophenyl carbonate. It was confirmed that the resulting compound had the aforementioned structure represented by the formula (11) by measuring with $^1$H-NMR. The measurement results are shown below.

Yield: 67%

Melting point: 149-150° C.

$^1$H-NMR (270 MHz, CDCl$_3$) δ (ppm): 3.99 (3H, s, OCH$_3$), 4.03 (3H, s, OCH$_3$), 5.72 (2H, s, CH$_2$), 7.11 (1H, s, ArH), 7.42 (2H, d, J=8.9 Hz, ArH), 7.77 (1H, s, ArH), 8.30 (2H, d, J=8.9 Hz, ArH)

(A-2) The photo base generating agent PBG-2 was synthesized according to the formula (12) below.

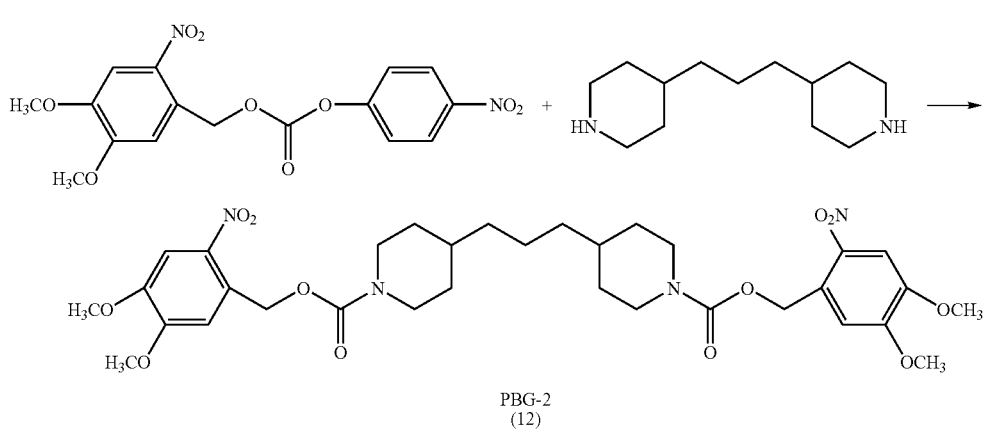

PBG-2
(12)

5.0 g (13.2 mmol) of 2-nitro-4,5-dimethoxybenzyl-4'-nitrophenyl carbonate synthesized according to the formula (11) and 0.55 g of 1-hydroxybenzotriazole were dissolved in 200 mL of dehydrated dichloromethane, and the solution was refluxed under an argon atmosphere. Thereafter, a dichloromethane solution of 1,3-di(4-piperidyl)propane (5.45 g (23.7 mmol)/80 mL) was slowly added dropwise thereto, followed by refluxing for 5 hours. The solution was washed with a saturated sodium hydrogen carbonate aqueous solution and then saline. The organic layer was dried over anhydrous magnesium sulfate and then distilled off. A yellow solid obtained by drying under reduced pressure was washed by stirring in a large amount of methanol. The resulting yellow precipitate was filtered by suction, and dried under reduced pressure to obtain PBG-2. It was confirmed that the resulting compound PBG-2 had the aforementioned structure represented by the formulae (10) and (12) by measuring with $^1$H-NMR. The measurement results are shown below.

[PBG-2]

Yield: 51%

$^1$H-NMR (270 MHz, CDCl$_3$) δ (ppm): 1.0-1.9 (16H, m, CH, CH$_3$), 2.6-3.0 (4H, m, N—CH$_2$), 3.97 (3H, s, OCH$_3$), 4.00 (3H, s, OCH$_3$), 4.1-4.3 (4H, m, N—CH$_2$), 5.51 (4H, s, Ar—CH$_3$), 6.98 (2H, s, ArH), 7.69 (2H, s, ArH)

(Epoxy Compound)

As the epoxy compound, a compound PGMA represented by the formula (13) below, a compound YDCN-701 represented by the formula (14) below or a compound EX-622 represented by the formula (15) below was used.

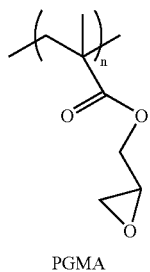

PGMA (13)

[Chem. 13]

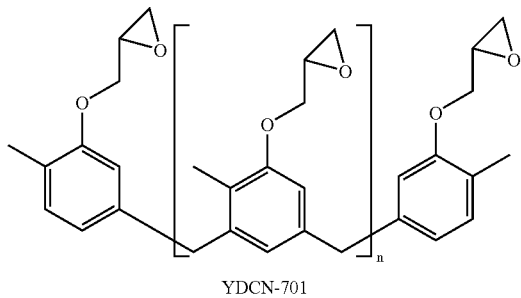

YDCN-701

(14)

[Chem. 14]

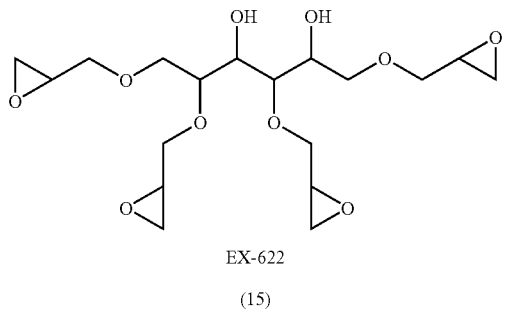

EX-622

(15)

[Chem. 15]

Evaluation of Base Multiplying Agents of Examples 1 and 2 and Comparative Example 1

The compounds Flu2 to Flu4 as the base multiplying agents obtained in Examples 1 and 2 and Comparative Example 1, the photo base generating agent, and the epoxy compound were dissolved in a solvent to obtain mixed solutions. The mixing ratios of the base multiplying agent, the photo base generating agent, the epoxy compound and the solvent were those shown in Tables 1 and 2 below.

The resulting mixed solution was spin-cast on a glass substrate under conditions of 1,000 rpm and 30 seconds. Thereafter, the coated solution was dried on a hot plate at 100° C. for 1 minute. The coated film was irradiated with monochrome light (13-15 mWcm$^{-2}$) of 365 nm for a prescribed period of time shown in Tables 1 and 2. Thereafter, the coated film was subjected to a heat treatment on a hot stage at a temperature (PEB temperature) shown in Tables 1 and 2 for a period of time (PEB time) shown in Tables 1 and 2. The coated film was then developed with propylene glycol 1-monomethyl ether 2-acetate (PEGMEA) for 30 seconds, and then washed with methanol.

The film forming property and the occurrence of curing (curing property) were visually confirmed. In order to facilitate confirmation of the film forming property and the occurrence of curing, the glass substrate was immersed in an ethanol solution of bromthymol blue for 10 minutes to dye the area having the film remaining. The film forming property and the curing property were evaluated by the following evaluation standard.

(Evaluation Standard for Film Forming Property)

good: A uniform film was formed.

poor: A uniform film was not formed.

(Evaluation Standard for Curing Property)

good: Only a part irradiated with light was uniformly cured.

poor: A part irradiated with light was not cured, or a part not irradiated with light was cured.

The results are shown in Tables 1 and 2 below.

TABLE 1

| | Test No. | | | | | | |
|---|---|---|---|---|---|---|---|
| | 1 | 2 | 3 | 4 | 5 | 6 | 7 |
| Base Multiplying Agent | Flu2 60 mg (200 mmol)*[1] | Flu3 91 mg (200 mmol)*[1] | | | Flu4 89 mg (200 mmol)*[1] | | |
| Photo Base Generating Agent | PBG-2 10 mg | PBG-2 10 mg | | | PBG-2 10 mg | | |
| Epoxy Compound | PGMA 100 mg | PGMA 100 mg | | | PGMA 100 mg | | |
| Spin-cast Solvent*[2] | CHCl$_3$/PEGMEA 10 wt. % | CHCl$_3$/PEGMEA 10 wt. % | | | CHCl$_3$/PEGMEA 10 wt. % | | |
| Irradiated Light (nm) | 365 nm | 365 nm | | | 365 nm | | |
| PEB Temperature (° C.) | 100° C. | 100° C. | | | 100° C. | | |
| PEB Time (min) | 10 | 10 | 20 | 30 | 10 | 20 | 30 |
| Light Irradiation Time (sec) | 120 | 160 | 90 | 60 | 210 | 110 | 80 |
| Irradiation Light Amount (mJcm$^{-2}$) | 1800 | 2100 | 1200 | 800 | 2700 | 1400 | 1000 |
| Film Forming Property | good | good | good | good | good | good | good |
| Curing Property (Occurrence of Curing) | poor (whole area cured) | good | good | good | good | good | good |

*[1] The molar amount of the base multiplying group is shown.
*[2] The temperature of the spin-cast solvent indicates the temperature of the epoxy compound in the solution.

TABLE 2

| | Test No. | | | | | | |
|---|---|---|---|---|---|---|---|
| | 8 | 9 | 10 | 11 | 12 | 13 | 14 |
| Base Multiplying Agent | none | Flu3 45 mg (100 mmol)*[1] | Flu4 45 mg (100 mmol)*[1] | none | Flu4 45 mg (100 mmol)*[1] | none | Flu4 45 mg (100 mmol)*[1] |
| Photo Base Generating Agent | PBG-2 10 mg | PBG-2 10 mg | PBG-2 10 mg | PBG-2 10 mg | PBG-2 10 mg | PBG-2 10 mg | PBG-2 10 mg |
| Epoxy Compound | PGMA 100 mg | PGMA 100 mg | PGMA 100 mg | YDCN-701 100 mg | YDCN-701 100 mg | EX-622 100 mg | EX-622 100 mg |
| Spin-cast Solvent*[2] | CHCl$_3$/ PEGMEA 10 wt. % | CHCl$_3$/ PEGMEA 10 wt. % | CHCl$_3$/ PEGMEA 10 wt. % | CHCl$_3$/ PEGMEA 10 wt. % | CHCl$_3$/ PEGMEA 10 wt. % | CHCl$_3$/ PEGMEA 10 wt. % | CHCl$_3$/ PEGMEA 10 wt. % |
| Irradiated Light (nm) | 365 nm | 365 nm | 365 nm | 365 nm | 365 nm | 365 nm | 365 nm |
| PEB Temperature (° C.) | 130° C. | 130° C. | 130° C. | 130° C. | 130° C. | 130° C. | 130° C. |
| PEB Time (min) | 15 | 15 | 15 | 15 | 15 | 15 | 15 |
| Light Irradiation Time (sec) | 21 | 0.6 | 0.6 | 2500 | 11 | 5000 | 30 |
| Irradiation Light Amount (mJcm$^{-2}$) | 14 | 14 | 14 | 50000 | 220 | 10000 | 600 |
| Film Forming Property | poor | good | good | poor | good | poor | good |
| Curing Property (Occurrence of Curing) | poor | good | good | poor (not cured) | good | poor (not cured) | good |

*[1] The molar amount of the base multiplying group is shown.
*[2] The temperature of the spin-cast solvent indicates the temperature of the epoxy compound in the solution.

The invention claimed is:

1. A base multiplying agent represented by the following formula (1):

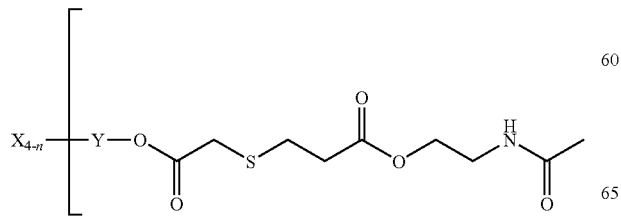

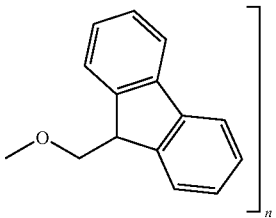

wherein in the formula (1), X represents a hydrogen atom, a substituted alkyl group or an unsubstituted alkyl group; Y represents a substituted or unsubstituted alkylene chain; and n represents an integer of from 1 to 4.

2. The base multiplying agent according to claim 1, wherein in the formula (1), Y represents a methylene chain.

3. The base multiplying agent according to claim 1, wherein in the formula (1), X represents an ethyl group.

4. The base multiplying agent according to claim 1, wherein in the formula (1), n represents 3.

5. The base multiplying agent according to claim 1, wherein in the formula (1), n represents 4.

6. A base-reactive curable composition characterized by comprising the base multiplying agent according to one of claims 1 to 5, a base generating agent, and a curable compound cured by action of a base.

7. The base-reactive curable composition according to claim 6, wherein the curable compound is an epoxy compound.

8. The base-reactive curable composition according to claim 7, wherein the epoxy compound is a liquid epoxy resin.

9. The base-reactive curable composition according to claim 6, wherein the base generating agent is a photo base generating agent generating a base by irradiation of light.

* * * * *